United States Patent [19]

Duncan

[11] Patent Number: 4,792,699
[45] Date of Patent: Dec. 20, 1988

[54] FIBER OPTIC PHOTOELECTRIC SENSOR WITH LIQUID REMOVING MEANS

[75] Inventor: Eugene F. Duncan, Wauwatosa, Wis.

[73] Assignee: Eaton Corporation, Cleveland, Ohio

[21] Appl. No.: 110,604

[22] Filed: Oct. 22, 1987

Related U.S. Application Data

[63] Continuation of Ser. No. 928,756, Nov. 10, 1986, abandoned.

[51] Int. Cl.$^4$ ............................................. G01N 15/06
[52] U.S. Cl. ..................................... 250/577; 250/227
[58] Field of Search ............... 250/227, 239, 573, 577; 73/293; 328/4; 350/96.2, 96.21, 96.22

[56] References Cited

U.S. PATENT DOCUMENTS 4,505,539  3/1985  Auracher et al. ................. 350/96.2
4,606,226  8/1986  Krohn ............................. 73/293

Primary Examiner—David C. Nelms
Assistant Examiner—Stephone B. Allen
Attorney, Agent, or Firm—L. G. Vande Zande

[57] ABSTRACT

A liquid removing attachment (22,24) for a fiber optic photoelectric sensor (14) that is used in a wet environment such as near a workpiece or tool (20) that is being sprayed or flowed with a liquid coolant. Such coolant produces an ambient mist or splash of liquid at the adjacent end of the fiber optic cable (16,18) which condenses or accumulates as a liquid mass or drops (6) on the exposed end of the optical fiber bundle (7) tending to interfere with light transmission therethrough. The attachment (22,24) provides radial channels (8b–e) adjacent the exposed ends of the optical fibers (7) that through adhesion of the liquid thereto together with the force of gravity cause such liquid mass or drops (6) to flow away thereby to reduce the liquid accumulation in the light transmission path.

17 Claims, 2 Drawing Sheets

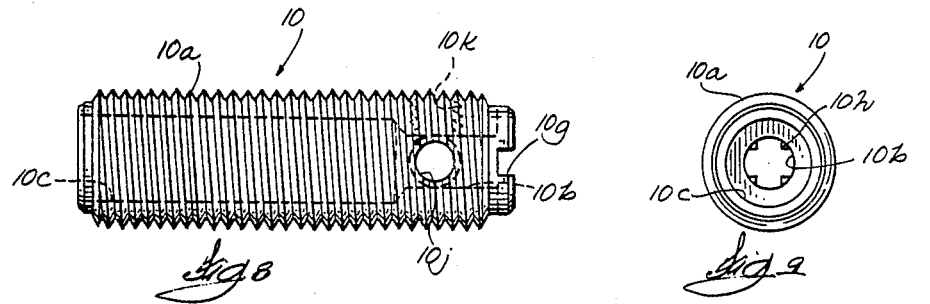
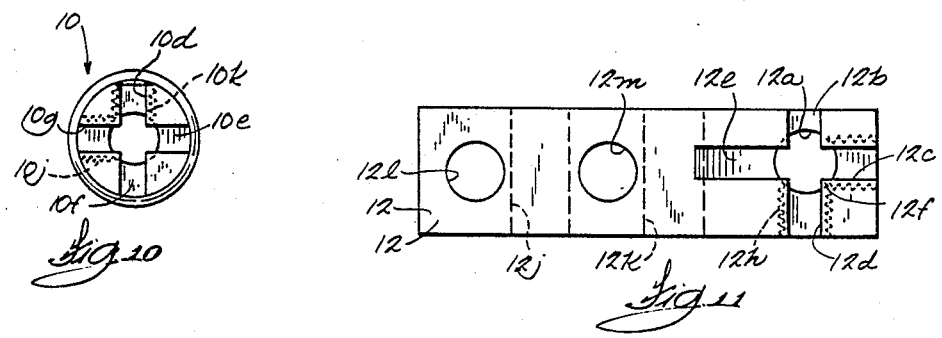
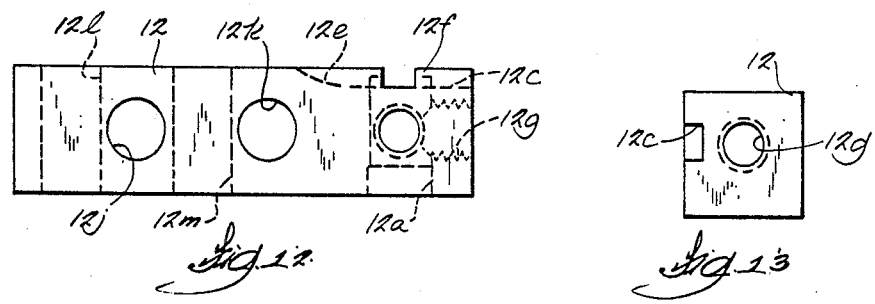
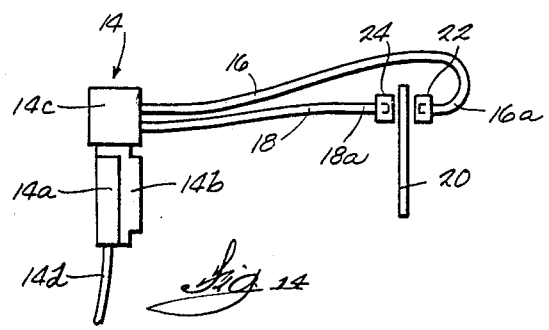

FIBER OPTIC PHOTOELECTRIC SENSOR WITH LIQUID REMOVING MEANS

This is a continuation of application Ser. No. 6,928,756, filed Nov. 10, 1986, now abandoned.

BACKGROUND OF THE INVENTION

Fiber optic photoelectric sensors have been known heretofore. Such photoelectric sensors commonly have a fiber optic cable one end of which is attached to the transmitter-receiver at the sensor head and the other end of which has exposed optical fiber ends positioned near the object to be sensed. However, when used in wet environments such as near a work piece or tool that is being sprayed or flowed with a liquid coolant, such fiber optic photoelectric sensors have been handicapped by reason of the moisture laden air or splash that condenses or accumulates as a liquid mass or drop on the adjacent end of the exposed optical fibers, tending to interfere with the passage of light signals therethrough. Consequently, it has been found desirable to improve such fiber optic photoelectric sensors by providing means for removing any liquid mass or drops forming at the exposed optical fiber enss of the cable. This invention relates to such improvements.

SUMMARY OF THE INVENTION

An object of the invention is to provide an improved fiber optic photoelectric sensor.

A more specific object of the invention is to provide a fiber optic photoelectric sensor cable with improved means for removing accumulation of liquid mass at the exposed ends of the optical fibers so as to avoid interference with the accurate passage of light signals therethrough.

Another specific object of the invention is to provide a fiber optic cable of a photoelectric sensor with readily attachable means at the remote end portion thereof for effectively removing any liquid mass or drop accumulating thereat in a wet environment so as to prevent interference with passage of light therethrough.

Another specific object of the invention is to provide a fiber optic cable of a photoelectric sensor that is used in a wet environment with improved means for removing liquid mass or drop accumulation at the exposed ends of the optical fibers and which can be added without any modification of the optical fiber cable.

Other objects and advantages of the invention will hereinafter appear.

BRIEF DESCRIPTION OF THE DRAWINGS

FIG. 8 is a side view of a modified liquid mass removing device formed integrally on the end of an adjustable bushing designed to fit on the end of the largest common size of fiber optic cable.

FIG. 9 is a left end view of the device of FIG. 8 showing the internal bore therein which receives the fiber optic cable.

FIG. 10 is a right end view of the device of FIG. 8 showing the liquid mass removing means formed thereon.

FIG. 11 is a front view of a modified liquid mass removing means to which the remote end of a fiber optic cable may be attached and which also serves as a support for the fiber optic cable.

FIG. 12 is a side view of the combined support and liquid mass removing means of FIG. 11.

FIG. 13 is a right end view of the modified liquid mass removing means of FIG. 11.

FIG. 14 is a schematic illustration of a sensor system showing application of the liquid mass removing means of FIGS. 5-7.

DESCRIPTION OF THE PREFERRED EMBODIMENTS

Figure 2:
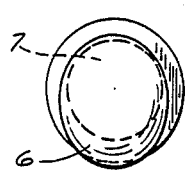
FIG. 2 is a right end view of the fiber optic cable of FIG. 1.
Figure 1:
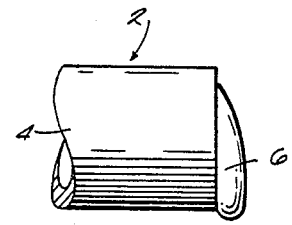
FIG. 1 is a fragmentary side view of the remote end portion of a prior art fiber optic cable showing an accumulated liquid mass or drop of liquid at the end thereof.

Referring to FIGS. 1 and 2, there is shown the remote end portion or scanner tip 2 of a fiber optic photoelectric sensor cable as commonly used in the prior art. This end portion 2 commonly comprises a metal sleeve or housing 4 that encloses a bundle of optical fibers 7 with their ends exposed as shown in FIG. 2 so that some of these fibers can emit light and others of these fibers can receive light reflected from an object to be detected. When a sensor of this type is used in a wet environment such as near a workpiece or tool that is being sprayed or flowed with a liquid coolant, there is produced an ambient mist or splash that accumulates or condenses at the end of the cable as a liquid mass or drop 6 that might partially or wholly cover the exposed ends of the optical fibers as shown in FIGS. 1 and 2. This liquid mass or drop 6 will tend to interfere with the passage of light signals from the end of the cable to the object as well as reflected light signals from the object back to the ends of the optical fibers in the cable. This invention overcomes this problem as hereinafter described.

Figure 3:
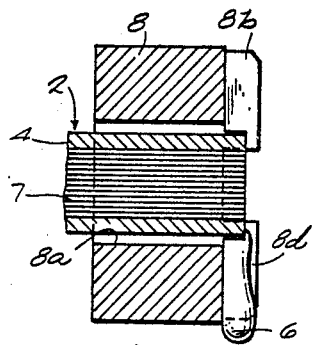
FIG. 3 is a fragmentary cross sectional view of the remote end portion of a fiber optic cable with a liquid mass removing device mounted thereon and showing a liquid mass or drop having been removed from the end of the cable.
Figure 4:
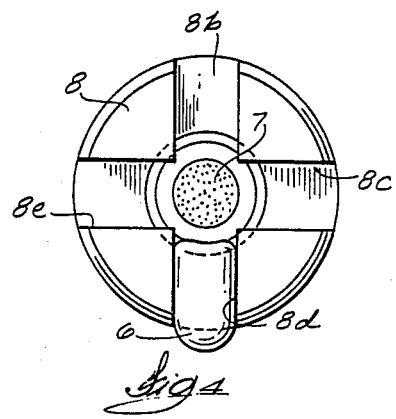
FIG. 4 is a right end view of the cable end liquid mass removing device of FIG. 3.

FIGS. 3 and 4 show a first version of means for removing the liquid mass or drop 6 from the exposed ends of the optical fibers at the end of the cable. This means comprises a liquid removing attachment 8 mounted at the remote end portion of the fiber optic cable. As shown in FIG. 3 the fiber optic cable includes at its remote end portion a metal sleeve or housing 4 filled with optical fibers 7 as in FIGS. 1 and 2. Liquid removing attachment 8 may be made from a stainless steel rod or the like and comprises a generally annular member having a central bore 8a therethrough so that it can be slipped onto the end portion 2 of the fiber optic cable and secured thereon by suitable means. As shown in FIG. 4, liquid removing attachment 8 is provided with angularly spaced radial grooves or channels 8b, 8c, 8d and 8e extending in vertical and horizontal directions from its center bore for conducting the accumulated liquid away from the exposed ends of the optical fibers. Gravity and adhesion forces cause the fluid drop 6 to be attracted down to avoid obstruction of the exposed ends of the optical fibers 7. These grooves 8b–8e are preferably rectangular in cross section so that adhesion to the surfaces of these grooves attracts the liquid away from the end of the cable at the center as shown in FIG. 4. As shown in FIG. 3, the sides of the channels or grooves such as 8b and 8d extend out beyond the end of cable 2 so that these sides will contact the fluid accumulating at the exposed ends of the optical fibers and through adhesion and gravity forces will cause such fluid to flow away therefrom.

Figure 5:
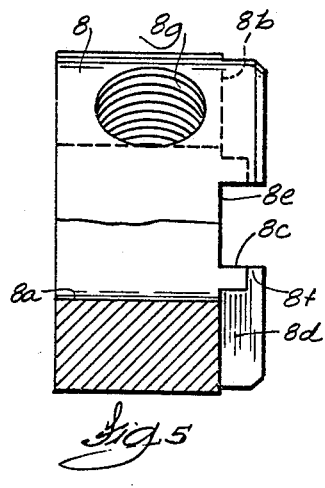
FIG. 5 is a side view of the liquid mass removing device that was shown rather schematically in FIGS. 3 and 4, partly in section to show the construction thereof.
Figure 6:
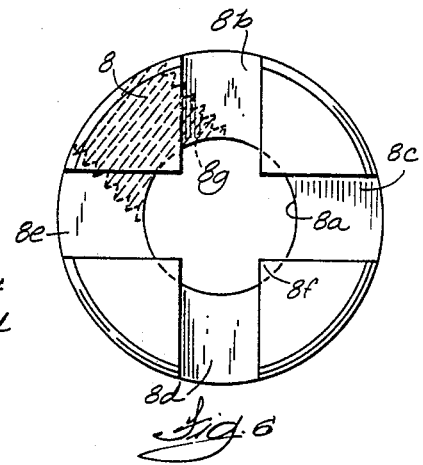
FIG. 6 is a right end view of the liquid mass removing device of FIG. 5.
Figure 7:
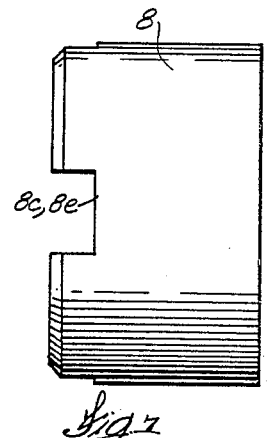
FIG. 7 is a right side view of the end portion of the liquid mass removing device of FIG. 6 showing the liquid removing groove therein, this device being designed for attachment to the end portion of the fiber optic cable.

FIGS. 5, 6 and 7 show construction details of a liquid removing adapter like that shown rather schematically in FIGS. 3 and 4. In FIGS. 5–7, reference characters like those used in FIGS. 3 and 4 will be used for like parts. As shown in FIG. 5, attachment device 8 is generally annular in configuration and is provided with a bore 8a therethrough for receiving the remote end of the fiber optic cable as hereinbefore mentioned. Radially extending upper and lower grooves 8b and 8d and right-hand and left-hand grooves 8c and 8e are provided in the forward end of this attachment for causing the liquid to flow away from the end of the cable. Angularly spaced grooves are provided so as to allow any angular orientation of the cable after mounting of device 8 thereon. These radial grooves are of such a width that the right angle points 8f between adjacent grooves extend part way inwardly of bore 8a so as to contact the liquid drop that accumulates at the end of the cable and cause it to flow away therefrom. As shown in FIG. 5, these points 8f are thinner in the axial direction of the attachment than the depth of grooves 8b–8e so that the end of the cable will extend part way into grooves or channels 8b–8e against the inner surfaces of these points 8f for more effective removal of the liquid from the end of the cable. A tapped hole 8g extends from the outer wall of attachment 8 into bore 8a for receiving a set screw or the like to rigidly secure the attachment to outer sleeve or housing 4 of the cable.

FIG. 7 shows an external side view of attachment 8. As shown therein, horizontal grooves 8e and 8c of like depth extend all the way across the end of attachment 8.

From the foregoing it will be apparent that to assemble attachment device 8 onto a fiber optic cable, it is only necessary to insert the end of the cable into bore 8a until it abuts points 8f and then thread a set screw (not shown) into tapped hole 8g and tighten the same to rigidly secure the attachment device to the cable.

FIGS. 8, 9 and 10 show a modification of the liquid removing means hereinbefore described in connection with FIGS. 5, 6 and 7. This modified version of the liquid removing means is also arranged to be attached to the remote end of a fiber optic cable but in addition includes mounting means so that it can be rigidly mounted in relation to an object to be sensed. As shown in FIG. 8, this modified version comprises an adjustable bushing 10 preferably made from a stainless steel rod or the like and having an external thread 10a along its length for receiving a pair of nuts (not shown) whereby this bushing may be mounted in relation to an object to be sensed. This bushing 10 has a bore therethrough having a first diameter 10b at its forward end for receiving the remote end portion of a fiber optic cable as hereinbefore described in connection with FIGS. 5, 6 and 7 and a larger diameter 10c extending rearwardly therefrom all the way through the rear end of the bushing for accommodating the largest diameter standard size of fiber optic cable. The forward end of this bushing is provided with the radial grooves 10d, 10e, 10f and 10g as well as the inwardly projecting right angle points 10h between adjacent grooves similar to those described in connection with the first version in FIGS. 5, 6 and 7. A pair of tapped holes 10j and 10k extend from its outer cylindrical surface inwardly at right angles to one another into the smaller diameter forward end 10b of the bore for receiving set screws to rigidly secure this adjustable bushing to the fiber optic cable. As will be apparent, this modified version of adjustable bushing can also be slid onto the remote end of a fiber optic cable and then a pair of set screws inserted and turned into tapped holes 10j and 10k to rigidly secure this bushing to the cable. A pair of nuts (not shown) may then be threaded onto the external thread 10a of this bushing for rigidly securing the same to a support in operative relation to the path or position of the article to be sensed.

FIGS. 11, 12 and 13 show a third modified version of the liquid removing means of the invention. As shown therein, this version comprises a support bar 12 having a transverse bore 12a extending almost through one end thereof and four grooves or channels 12b, 12c, 12d and 12e extending radially at 90° angles from the center line of the inner end of bore 12a. Three of these grooves 12b, 12c and 12d extend all the way to the edge of the bar while groove 12e extends part way along the length thereof gradually curving to the surface thereof. Right angle points such as 12f between adjacent grooves also extend inwardly or toward one another into the area of bore 12a as in FIGS. 6 and 10 to assist in contacting and leading the liquid away from the end of the cable and along the grooves. A first tapped hole 12g extends from the end of the support bar into bore 12a for receiving a set screw whereby to secure the cable in the bore. Another tapped hole 12h extends from one side of the support bar into bore 12a for receiving another set screw for securing the cable in the bore. As shown in FIGS. 11 and 12, the remainder of the length of the support bar 12 is provided with two pairs of spaced holes 12j, 12k and 12m, 12n at right angles to one another for receiving mounting elements such as bolts, screws or the like for mounting the support bar and the fiber optic cable carried thereby in relation to an object to be sensed.

FIG. 14 schematically shows a fiber optic photoelectric sensor switch system arranged in relation to an object to be sensed. As shown in FIG. 14, the sensor switch 14 is of the modular type having a receptacle module 14a, a body module 14b and a sensor head module 14c secured to one another in conventional manner with an electrical conductor or conductors 14d extending out from receptacle module 14a for connection to electrical power and to a device to be controlled. Modules of this type for a solid state limit switch generally are shown in my prior U.S. Pat. No. 4,412,129 dated Oct. 25, 1983. A pair of fiber optic cables 16 and 18 extend from sensor head 14c with their remote ends 16a and 18a being positioned on opposite sides of an object 20 to b sensed. A pair of liquid removing devices 22 and 24 are mounted on the remote ends of fiber optic cables 16 and 18, respectively, these liquid removing devices being generally similar to those described in connection with FIGS. 3–7. In this arrangement, it may be assumed that fiber optic cable 16 is connected to a light transmitter and that fiber optic cable 18 is connected to a light receiver in sensor head 14c. Consequently, when object 20 either interrupts or reestablishes the light radiation from cable 16 to cable 18, a signal will be received in sensor head 14c to perform the desired function. Liquid removing devices 22 and 24 prevent liquid mass or drops accumulating on the exposed ends of the optical fibers so as not to interfere with the light transmission therethrough.

While several versions of attachment devices constituting liquid removing means have been illustrated and described, it will be apparent that such liquid removing means could alternatively be made integral with the short metal sleeve or tip commonly used at the remote end of a flexible fiber optic cable.

While the apparatus hereinbefore described is effectively adapted to fulfill the objects stated, it is to be understood that the invention is not intended to be confined to the particular preferred embodiments of fiber optic photoelectric sensor with liquid removing means disclosed, inasmuch as they are susceptible of various modification without departing from the scope of the appended claims.

I claim:

1. In a fiber optic photoelectric sensor having a housing enclosing photoelectric means and fiber optic cable means having a local end portion mounted on said housing in operative relation to said photoelectric means therein and a remote end portion exposing optical fiber ends mounted in operative relation to an object to be sensed, said remote end portion being in a wet environment such as near a workpiece or tool that is being sprayed or flowed with liquid coolant which produces an ambient mist or splash at said remote end portion that accumulates or condenses as a liquid mass or drop on said remote end portion tending to interfere with passage of light signals thereat, the improvement comprising:

liquid removing means at said remote end portion of said fiber optic cable means for causing said liquid mass to flow away from said ends of said optical fibers at said remote end portion so as to prevent such accumulation of said liquid as to significantly interfere with the passage of light signals therethrough.

2. In the fiber optic photoelectric sensor claimed in claim 1, wherein:

said photoelectric means comprises a phoooelectric transmitter and receiver;

said fiber optic cable means comprises a first fiber optic cable extending from said transmitter to one side of said object to be sensed and a second fiber optic cable extending from the other side of said object to be sensed to said receiver;

and said extension is provided at said remote end of each of said cables.

3. In the fiber optic photoelectric sensor claimed in claim 1, wherein:

said photoelectric means comprises a photoelectric transmitter and receiver;

said fiber optic cable means comprises a single cable having first and second branches at said local end portion in operative relations to said transmitter and receiver, respectively, and a third branch at said remote end portion containing fibers conducting transmitted light and fibers conducting reflected and received light inoperative relation to said object to be sensed;

and said extension is provided at the end of said third branch.

4. In the fiber optic photoelectric sensor claimed in claim 1, wherein:

said liquid removing means comprises means providing an extension surrounding said remote end portion of said fiber optic cable means extending out beyond said ends of said optical fibers;

and radial grooves in said extension having surfaces that through adhesion of said liquid thereto together with the force of gravity reduce the liquid accumulation at said exposed ends of said optical fibers.

5. In the fiber optic photoelectric sensor claimed in claim 1 wherein:

said liquid removing means comprises means providing an extension at said remote end portion of said fiber optic cable means extending out beyond said ends of said optical fibers;

and a groove in said extension having surfaces that through adhesion of said liquid thereto together with the force of gravity cause said liquid to flow away to reduce the liquid mass accumulation at said exposed ends of said optical fibers.

6. In the fiber optic photoelectric sensor claimed in claim 4, wherein:

said grooves extend in angularly spaced directions.

7. In the fiber optic photoelectric sensor claimed in claim 4, wherein:

said liquid removing means comprises points between the inner ends of said radial grooves overlying the said remote end of said fiber optic cable for contacting the liquid mass or drop thereat and leading it away along one of said grooves.

8. In the fiber optic photoelectric sensor claimed in claim 5, wherein:

said extension is an attachment rigidly secured to said remote end portion of said fiber optic cable means.

9. In the fiber optic photoelectric sensor claimed in claim 5, wherein:

said extension is part of a supporting member used for supporting said remote end portion of said cable means.

10. In the fiber optic photoelectric sensor claimed in claim 5, wherein:

said extension is integral with said remote end portion of said cable means.

11. In the fiber optic photoelectric sensor claimed in claim 5, wherein;

said extension is a generally annular member rigidly secured to and supported by said remote end portion of said cable means.

12. A fiber optic cable having a first end mounted in operative relation to photoelectric apparatus and an end remote from said apparatus exposing optical fiber ends to an object to be sensed by light signals emitted or received at said optical fiber ends, and liquid removing means at said remote end comprising means extending beyond said optical fiber ends and having groove communicating with said optical fibers ends, said groove having surfaces which effect adhesion of said liquid thereto, said adhesion and gravitational force causing said liquid to flow away from said optical fiber ends preventing an accumulation of liquid on said optical fiber ends.

13. The fiber optic cable claimed in claim 12, wherein:

said means extending beyond said optical fiber ends comprises an attachment surrounding said remote end of said fiber optic cable and secured thereto.

14. The fiber optic cable claimed in claim 12, wherein:
said means extending beyond said optical fiber ends comprises means surrounding said remote end of said fiber optic cable; and
said groove comprises a downwardly disposed one of a plurality of grooves extending radially from said optical fiber ends in said surrounding means.

15. The fiber optic cable claimed in claim 14, wherein:
said means surrounding said remote end of said fiber optic cable comprises a part of a surrounding member for said remote end.

16. The fiber optic cable claimed in claim 14, wherein:
said plurality of grooves establish points at junctures of inner ends thereof, said points overlying said remote end of said fiber optic cable and contacting liquid formed at said remote end and leaving said liquid away along said one of said grooves.

17. The fiber optic cable claimed in claim 15, wherein:
said means surrounding said remote end of said fiber optic cable comprises an attachment disposed over said remote end and secured to said fiber optic cable.

* * * * *